(12) United States Patent
Kuester

(10) Patent No.: US 11,051,732 B2
(45) Date of Patent: Jul. 6, 2021

(54) LANCING DEVICES

(71) Applicant: MARLDELL LIMITED, Petersfield (GB)

(72) Inventor: Steve Kuester, Oxfordshire (GB)

(73) Assignee: Marldell Limited, Petersfield (GB)

( * ) Notice: Subject to any disclaimer, the term of this patent is extended or adjusted under 35 U.S.C. 154(b) by 126 days.

(21) Appl. No.: 16/492,822

(22) PCT Filed: Mar. 9, 2018

(86) PCT No.: PCT/GB2018/050615
§ 371 (c)(1),
(2) Date: Sep. 10, 2019

(87) PCT Pub. No.: WO2018/162930
PCT Pub. Date: Sep. 13, 2018

(65) Prior Publication Data
US 2020/0138354 A1    May 7, 2020

(30) Foreign Application Priority Data
Mar. 10, 2017 (GB) ..................................... 1703833

(51) Int. Cl.
*A61B 5/151* (2006.01)
*A61B 5/15* (2006.01)

(52) U.S. Cl.
CPC ....... *A61B 5/15111* (2013.01); *A61B 5/15117* (2013.01); *A61B 5/15142* (2013.01); *A61B 5/150412* (2013.01); *A61B 5/150549* (2013.01); *A61B 5/150717* (2013.01); *A61B 5/150885* (2013.01)

(58) Field of Classification Search
CPC .......... A61B 5/150549; A61B 5/15144; A61B 5/150885; A61B 5/15142; A61B 5/15111; A61B 5/150412; A61B 5/15117; A61B 5/150717
See application file for complete search history.

(56) References Cited

U.S. PATENT DOCUMENTS

| 5,707,384 A | 1/1998 | Kim |
| 2003/0050627 A1* | 3/2003 | Taylor .............. A61B 5/150022 606/1 |
| 2007/0162065 A1 | 7/2007 | Li et al. |

(Continued)

FOREIGN PATENT DOCUMENTS

| GB | 2 521 150 A1 | 6/2015 |
| WO | 03/026728 A1 | 4/2003 |
| WO | 2015/020609 A1 | 2/2015 |

*Primary Examiner* — Wade Miles
(74) *Attorney, Agent, or Firm* — Rodney J. Fuller; Booth Udall Fuller, PLC

(57) ABSTRACT

A single use lancing device comprising: a housing (10) defining a cavity; a needle assembly (12) comprising a needle (50) and a needle holder (52) and located within the cavity; a release member (16); and a spring (14) arranged to bias the needle assembly in a forward direction relative to the release member; wherein the release member comprises retaining arms (38) and is movable relative to the housing between a primed position in which the retaining arms are arranged to cooperate with the housing to restrain the needle assembly in a primed position, and a deployed position in which the restraining arms are arranged to release the needle assembly to deploy the needle.

12 Claims, 5 Drawing Sheets

(56) References Cited

U.S. PATENT DOCUMENTS

| | | | |
|---|---|---|---|
| 2012/0215246 A1* | 8/2012 | Hyoue | A61B 5/150022 |
| | | | 606/182 |
| 2013/0066353 A1 | 3/2013 | Hong | |
| 2014/0052023 A1 | 2/2014 | Starnes | |
| 2018/0206770 A1* | 7/2018 | Wight | A61B 5/15 |
| 2019/0275261 A1* | 9/2019 | Nickeson | A61B 5/150885 |

* cited by examiner

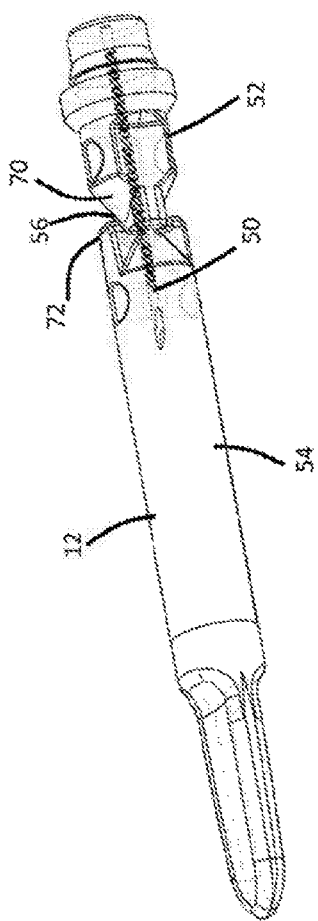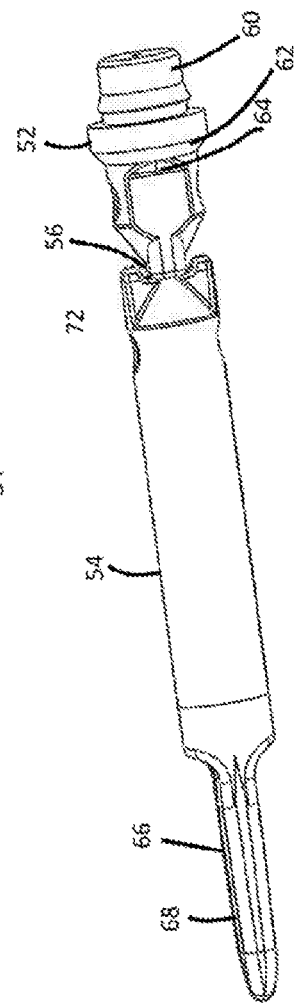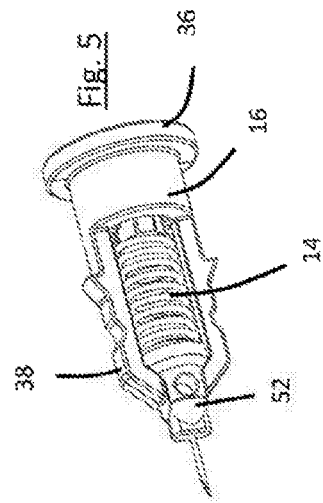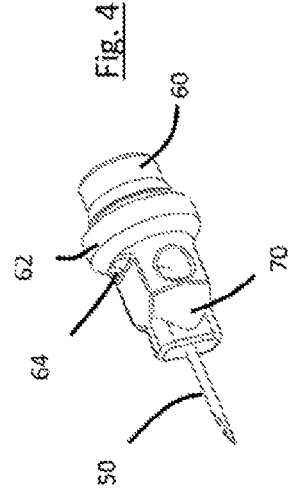

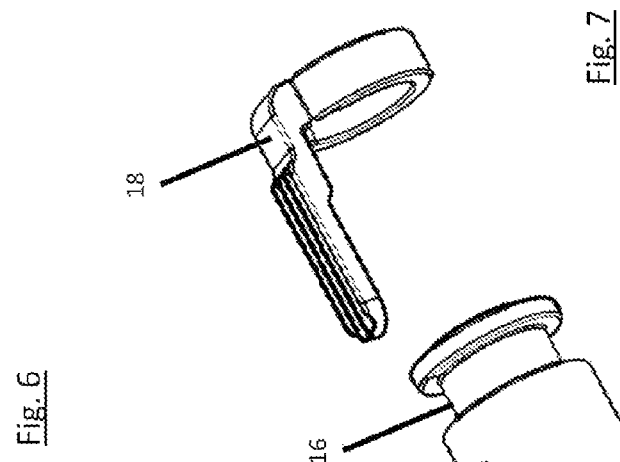
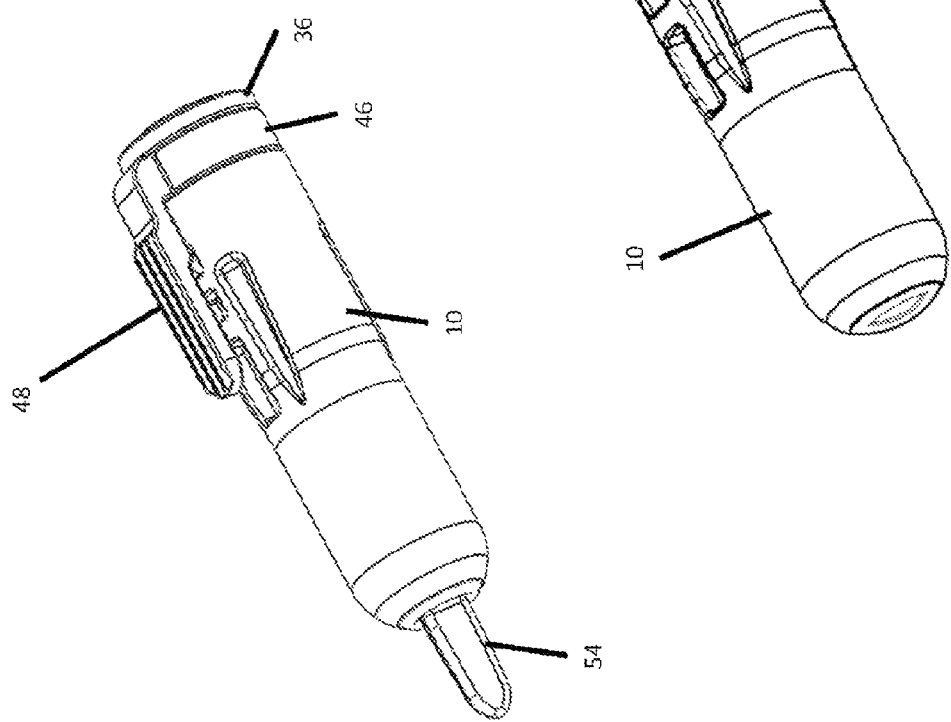

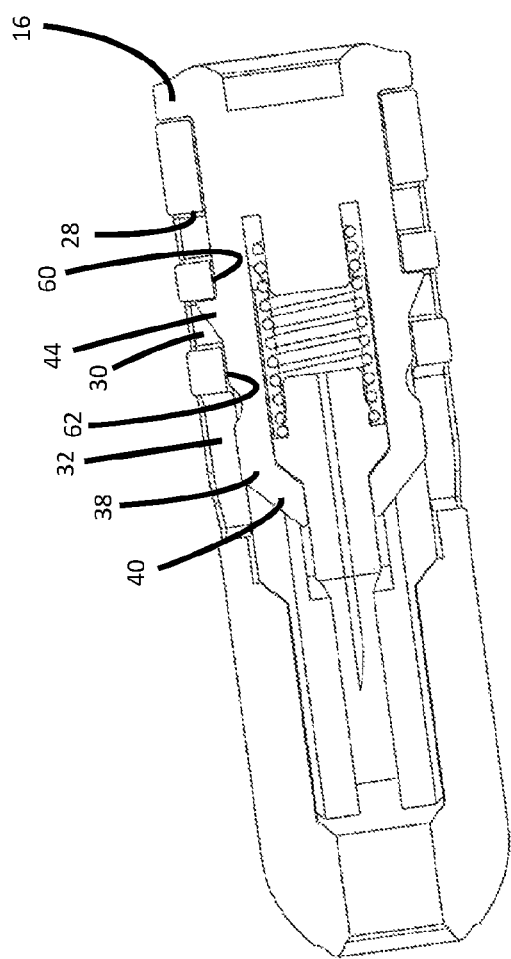

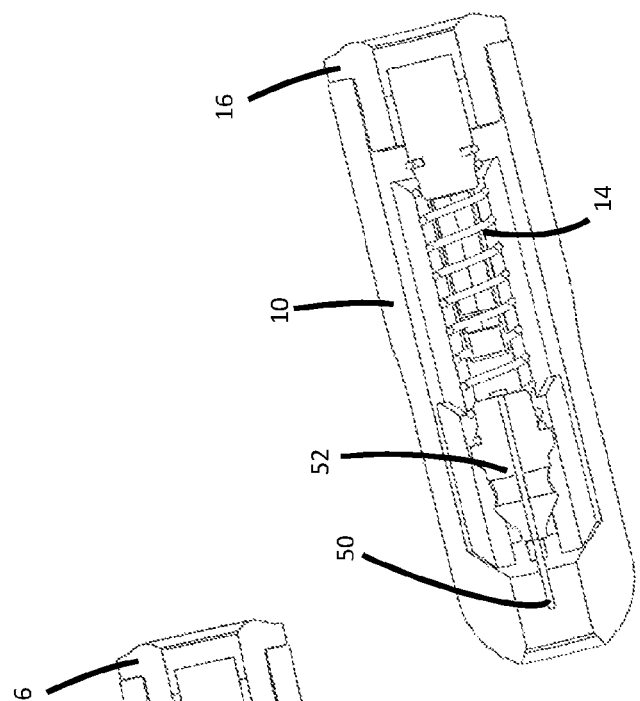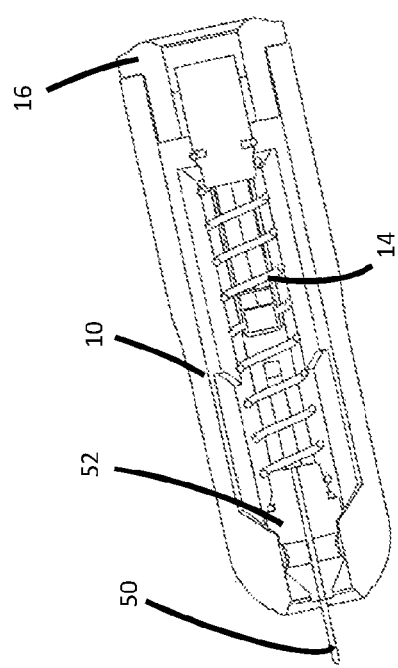

LANCING DEVICES

RELATED APPLICATION DATA

This application is the U.S. National Stage of International Application No. PCT/GB2018/050615, filed Mar. 9, 2018, which claims priority to Great Britain Application No. 1703833.2, filed Mar. 10, 2017, the contents of each of which are herein expressly incorporated by reference for all purposes in their entireties.

FIELD OF THE INVENTION

The present invention relates to lancing devices, in particular single use lancing devices with a lancet that is retracted into a shielded position after use.

BACKGROUND TO THE INVENTION

Lancing devices are commonly used both in medical facilities and by private individuals to obtain a blood sample from a subject by puncturing the skin of the subject. Lancets are used when only a small amount of blood is required. Subjects that have diseases such as diabetes use blood testing at regular intervals to monitor blood sugar levels, and many other diseases and conditions require small samples of blood to be taken, for example for monitoring or diagnostic purposes. Obtaining a sample of blood usually involves pricking the skin on a finger or other suitable body part with a lancet or needle. In view of blood-borne diseases, it is important that, after use of the lancet, parts of the lancet that have been in contact with blood do not then come into contact with other persons. Thus, an important aspect of lancing devices involves preventing the lancet or needle from wounding another person after the skin of the patient has been punctured. The lancet should therefore be shielded, after use of the device, to prevent accidental wounding of another person. Further, the lancing device should be disposable to reduce the possibility of disease transmission due to the device being used subsequently on other persons. In this respect, the lancet should preferably be a single use device with features to prevent reuse.

Contact activated lancets are known in the art. These devices have a needle holder and a triggering device enclosing a lancet structure. They are maintained in an armed position ready to be activated by pressure on the triggering device. Drawbacks of known lancing devices include the problem of accidentally triggering the lancet, either because the lancing device is designed to be triggered on contact with the skin or because the triggering device is activated accidently by the user before the lancet is correctly positioned on the skin. Many single use lancets are wasted because they are activated before they are in the correct position and therefore do not pierce the skin adequately to obtain a suitable blood sample.

Several prior art lancing devices attempt to overcome the problem of accidental triggering by including complicated arrangements for retaining and releasing the lancet within the structure of the lancing device. These complex arrangements require the lancing device to be comprised of many components, and therefore these lancets are often expensive or complicated to manufacture and are therefore not suitable for mass market use.

It is therefore desirable to provide a robust, disposable lancing device of simple construction which effectively reduces the likelihood of the lancet triggering accidentally.

SUMMARY OF THE INVENTION

According to a first aspect of the invention a lancing device comprises a housing defining a cavity; a needle assembly comprising a needle and a needle holder and located within the cavity; a release member; and a spring arranged to bias the needle assembly in a forward direction relative to the release member; wherein the release member comprises retaining arms and is movable relative to the housing between a primed position in which the retaining arms are arranged to cooperate with the housing to retain the needle assembly in a primed position, and a deployed position in which the retaining arms are arranged to release the needle assembly to deploy the needle.

The device may further comprise a needle cover arranged to cover the needle before use. The needle cover may be formed integrally with the needle holder. A shear portion may be provided between the needle holder and the cover so that the needle cover can be removed from the needle and needle holder.

When the release member is in the primed position, part of the cover may protrude from the front end of the housing, for example through a hole in the front end of the housing.

The needle cover may be arranged such that rotating the cover relative to the needle holder breaks the shear portion and allows the cover to be removed.

The spring may be maintained in a compressed state when the needle assembly is in the primed position. The spring may have a relaxed state in which the needle is retained completely within the housing.

The spring may be arranged, on deployment of the needle, to move to an extended state in which the needle projects from the front end of the housing, before returning to the relaxed state to retract the needle into the housing.

The lancing device may further comprise a removable safety member arranged to retain the release member in its primed position.

The housing may comprise a retaining surface arranged to retain the retaining arms in a retaining position when the release member is in its primed position. The housing may define openings into which the retaining arms can move to release the needle assembly when the release member is in the deployed position.

The lancing device may be sterilised and plastic over moulding may maintain the needle in a sterile condition until the shearable joint between the needle holder and the cover element is broken.

The lancing device may further comprise any one or more features of the embodiments of the invention which are shown by way of example only in the accompanying drawings as will now be described.

FIG. 2 is a perspective view of a needle assembly and needle cover forming part of the device of FIG. 1;

FIG. 3 is a further view of the needle assembly and needle cover of FIG. 2;

FIG. 4 is a perspective view of the needle assembly of FIG. 2 with the cover removed;

FIG. 5 is a perspective view of the needle assembly of FIG. 4 and a spring and release member of the device of FIG. 1;

FIG. 6 is a perspective view of the device of FIG. 1 in a primed condition;

FIG. 7 is a perspective view of the device of FIG. 1 with the safety member removed ready for deployment;

FIG. 8 is a longitudinal section through the device of FIG. 1 with the release member in a deployed position;

FIG. 9 is a longitudinal section through the device of FIG. 1 on a plane perpendicular to that of FIG. 8 with the release member in the deployed position and the needle assembly in a fully extended position; and FIG. 10 is a section similar to that of FIG. 9 with the needle assembly in a retracted position.

DESCRIPTION OF THE PREFERRED EMBODIMENTS

Figure 1:
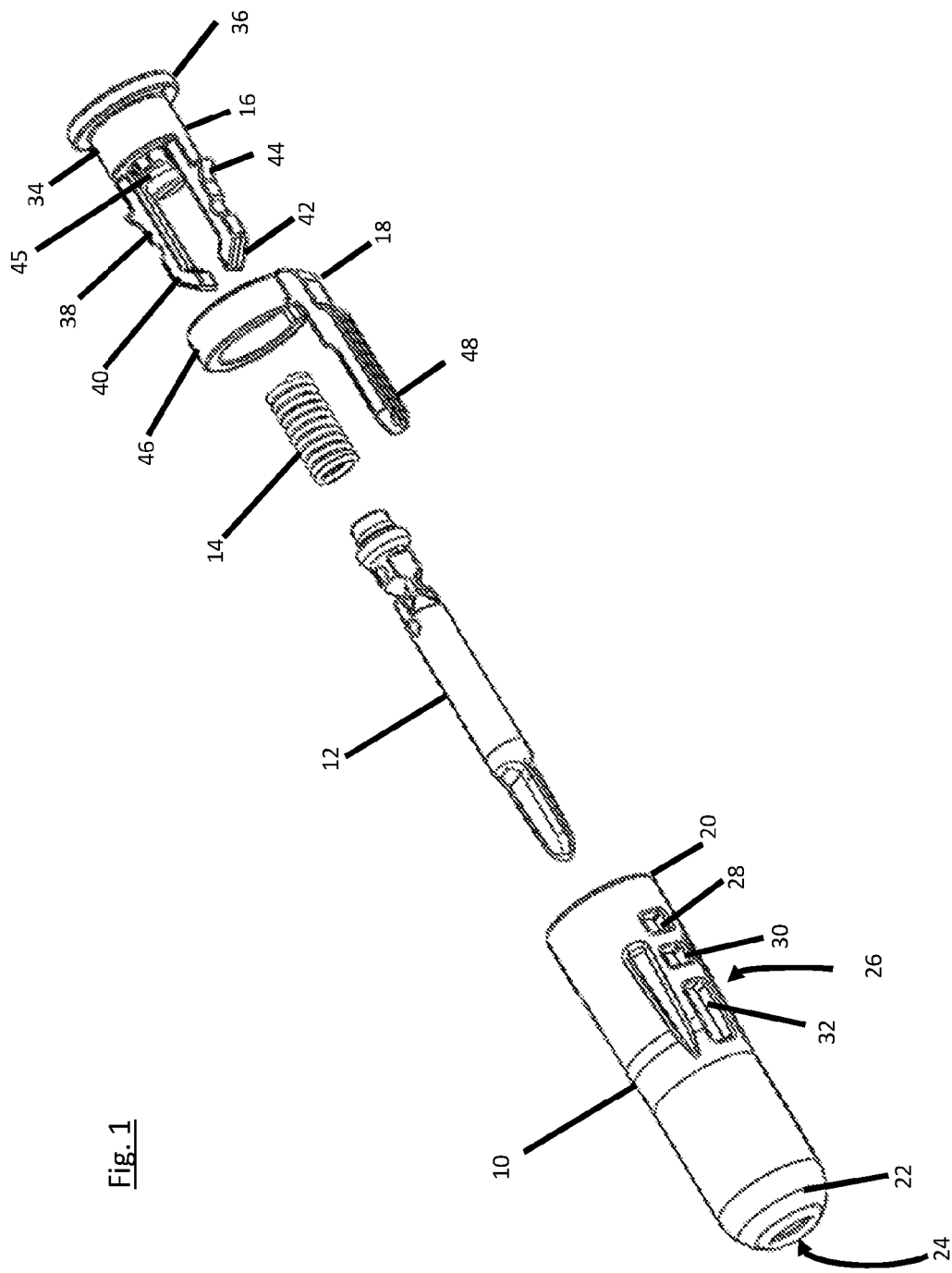
FIG. 1 is an exploded view of a lancing device according to an embodiment of the invention.

Referring to FIG. 1, the lancing device may comprise a housing 10, a needle and cover assembly 12, a spring 14, a release member 16 and a safety member 18. The housing 10 may be essentially cylindrical and may have an open rear end 20 and a front end 22, arranged for contact with the patient's skin, which is partially closed, for example by being partially domed, and may have an opening 24 in its centre. The housing 10 may also have a series of apertures 26 spaced axially along its side wall. These may include a first retaining aperture 28 and a second retaining aperture 30 which may be forward of the first, arranged to cooperate with the release member to retain the release member in a primed and a deployed position as will be described below. They may also include release apertures or pockets 32, which may be forward of the retaining apertures and may be arranged to allow release of the needle assembly as will also be described below. A corresponding further series of apertures may be provided on the opposite side of the housing 10. Instead of apertures that extend through the side wall of the housing 10, there may be retaining or release recesses on the inner surface of the side wall so that these are not visible from the outside of the housing 10. Also, instead of a helical spring 14 as shown, other types of spring may be used.

The release member 16 may comprise a cylindrical base portion 34 which is arranged to be a sliding fit inside the rear end 20 of the housing 10, a cap 36 extending radially from the rear end of the base portion 34, and a number of retaining arms 38, for example two, extending from the front end of the base portion 34. The retaining arms 38 may be flexible and resilient. They may comprise inwardly projecting retaining projections 40 on their front ends 42. The retaining arms may also each have a latching projection 44 on their outer sides, arranged to locate in the retaining apertures 28, 30 in the housing 10. The latching projections may have rear surfaces that are radial, i.e. perpendicular to the central longitudinal axis of the device. The latching projections may have tapered or sloping front surfaces. These surfaces may be arranged to allow the latching projections 44 to ride over part of the housing 10 when moving forwards, but to abut against surfaces on the housing to prevent return rearward movement of the release member. The release member 16 may further comprise a spring mounting 45, which may be cylindrical, and may project forwards from the base portion 34 between the retaining arms 38, so that the rear end of the spring 14 can fit over it.

The safety member 18 may comprise a plastic ring or collar 46 of the same diameter as the rear end 20 of the housing 10 and arranged to fit around the base portion 34 of the release member 16. The cap 36 of the release member may therefore abut against the safety member 18 when the safety member is in place, thereby preventing forward movement of the release member 16. The safety member may have a weakened shear or tear portion in the ring 46, and may further comprise a pull tab portion 48 allowing it to be easily torn off and removed.

Referring to FIGS. 2, 3 and 4, the needle and cover assembly 12 may comprise a needle 50 having its base supported in a needle holder 52. The needle holder may be of plastic material and moulded over the base of the needle 50. The assembly may further comprise a needle cover 54 which may be of the same material as the needle holder 52 and may be formed by over-moulding onto the needle at the same time as the needle holder. Indeed the needle holder 52 and cover 54 may be formed integrally with each other, with a shear portion 56 formed between them which can be broken to separate them and remove the cover 54 from the needle 50. The needle holder 52 may comprise a body 58 and may have a spring mounting 60 projecting from its rear end, which may be cylindrical and arranged so that the spring can fit over it. The needle holder 52 may have a tapered or otherwise shaped portion 62 having retaining surfaces 64 which are arranged to engage with the retaining projections 40 on the release member 16.

The needle cover 54 may be cylindrical and project forward from the front end of the needle 50. The front end 66 of the needle cover 54 may be flattened to form a grip portion 68 that can be easily held by a user such that the user can apply a twisting torque to the needle cover 54. Cam surfaces 70 on the needle holder 52 and cam projections 72 on the cover may be arranged to cooperate on rotation of the cover 54 relative to the needle holder to urge the cover 54 forwards away from the needle holder thereby aiding in the separation of the cover 54 from the needle holder 52.

Referring to FIG. 5, when the device is primed the needle holder 52 is held between the retaining arms 38 of the release member 16, with the retaining projections 40 located against the retaining surfaces 46 on the needle holder 52. The spring 14 has its rear end located over the spring mounting 45 on the release member, and its front end located over the spring mounting 60 on the needle holder. Therefore when the spring 14 is in compression it acts to urge the needle assembly forward relative to the release member 16.

Referring to FIGS. 6 to 10, operation of the embodiment shown will now be described. Operation of other embodiments may be the same where they include the same or corresponding features. When the device is assembled and stored it is in a primed condition as shown in FIG. 6. The needle may be sterilized, for example using gamma radiation before use. The needle and cover assembly is complete, with the front end 66 of the needle cover 54 projecting through the hole 24 in the front end of the housing 10. The safety member 18 is in place with its ring 46 around the body 34 of the release member 16. The retaining arms 38 are in their retaining position with the projections 40 resting against the needle holder 52 as shown in FIG. 5. The retaining arms 38 are prevented from moving apart because a part 60 of the housing between the first and second retaining apertures 28, 30, and a further part 62 of the housing between the second retaining aperture 30 and the release aperture 32, are located against the outer surface of each of the retaining arms 38. The latching projection 44 of each arm 38 is located in one of the first retaining apertures 28, since the release member 16 is still in its rearward primed position as shown in FIG. 6 rather than in the forward deployed position as shown in FIG. 8.

Referring to FIG. 7, to actuate the device and deploy the needle, the safety collar 18 is removed by pulling the tab 48, and the needle cover 54 is twisted and pulled to remove it from the needle 50. Then referring to FIG. 8, the release member 16 is then pushed forward into its deployed position. The central parts arms on which the projections 44 are formed flex inwards to allow the latching projections 44 to move forward and into the second retaining apertures 30 as shown in FIG. 8. When the latching projections 44 are aligned with the second retaining apertures 30 the arms 38 flex outwards again so that the latching projections 44 move into the apertures 30, where their rear surfaces prevent rearward movement of the release member away from the deployed position. The forward ends of the arms 38, including the retaining projections 40 are then aligned with the release apertures 32 in the housing 10, allowing the arms 38 to flex outwards to release the needle holder 52. The force of the spring 14 is then sufficient to push the needle holder 52 forward, urging the arms 38 apart so that the widest part of the needle holder 52 can pass between the ends of the arms 38. Thereafter the needle holder 52 is free to move forward under the force of the spring 14 and it accelerates forward until the spring reaches its natural length, from there the momentum of the needle assembly carries the needle forwards until the needle holder 52 contacts the front end of the housing 10 and the needle projects forwards of the front end of the housing as shown in FIG. 9. From this fully extended position the spring 16 then contracts again to its natural length at which it holds the needle holder 52 away from the front end of the housing 10 so that the full length of the needle 50 is within the housing 10 as shown in FIG. 10. This prevents the needle 50 from coming into contact with another person after use.

When the release member 16 is in the deployed position as shown in FIG. 8, the flat rear surfaces of the latching projections 44 abut against the rear surfaces of the second retaining apertures 30. This prevents the release member 16 from being pulled backwards, and therefore prevents re-use of the device.

It will be appreciated that some embodiments of the invention can provide a lancet device with improved reliability, which is cheap and simple to manufacture and assemble. The device may consist of only components, a housing, a lancet consisting of a needle over-molded with plastic, a spring, an actuator or release member, and a safety member or tear off. This is advantageous because it is cheaper and quicker to manufacture a small number of components, simple to assemble the components and the device is less susceptible to parts malfunctioning.

The invention claimed is:

1. A single use lancing device comprising:
a housing defining a cavity;
a needle assembly comprising a needle and a needle holder and located within the cavity;
a release member; and
a spring arranged to bias the needle assembly in a forward direction relative to the release member;
wherein the release member comprises retaining arms and is movable relative to the housing between a primed position in which the retaining arms are arranged to cooperate with the housing to restrain the needle assembly in a primed position, and a deployed position in which the restraining arms are arranged to release the needle assembly to deploy the needle, wherein the lancing device further comprises a needle cover which is formed integrally with the needle holder with a shear portion there between so that the needle cover can be removed from the needle and needle holder and a removable safety member arranged to retain the release member in its primed position.

2. The lancing device according to claim 1, wherein, when the release member is in the primed position, part of the cover protrudes through a hole in the front end of the housing.

3. The lancing device according to claim 2, wherein rotating the cover relative to the needle holder breaks the shear portion and allows the cover to be removed.

4. The lancing device according to claim 2, wherein the spring is maintained in a compressed state when the needle assembly is in the primed position, and has a relaxed state in which the needle is retained completely within the housing.

5. The lancing device according to claim 2, wherein the spring is arranged on deployment of the needle, to move to an extended state in which the needle projects form the front end of the housing, before returning to the relaxed state to retract the needle into the housing.

6. The lancing device according to claim 2, wherein the housing comprises a retaining surface arranged to retain the retaining arms in a retaining position when the release member is in its primed position, and defines openings into which the retaining arms can move to release the needle assembly when the release member is in the deployed position.

7. The lancing device according to claim 1, wherein rotating the cover relative to the needle holder breaks the shear portion and allows the cover to be removed.

8. The lancing device according to claim 1, wherein the spring is maintained in a compressed state when the needle assembly is in the primed position, and has a relaxed state in which the needle is retained completely within the housing.

9. The lancing device according to claim 1, wherein the spring is arranged on deployment of the needle, to move to an extended state in which the needle projects form the front end of the housing, before returning to the relaxed state to retract the needle into the housing.

10. The lancing device according to claim 1, wherein the housing comprises a retaining surface arranged to retain the retaining arms in a retaining position when the release member is in its primed position, and defines openings into which the retaining arms can move to release the needle assembly when the release member is in the deployed position.

11. The lancing device according to claim 1, further comprising a latching mechanism arranged to allow the release member to move into the deployed position, but to prevent movement of the release member from the deployed position back to the primed position.

12. The lancing device according to claim 11, wherein the latching mechanism comprises a latching projection arranged to urge at least one of the retaining arms inwards as the retaining member moves forwards, and when the release member reaches the deployed position to release said one of the retaining arms into a latched position in which rearward movement of the release member is prevented.

* * * * *